(12) United States Patent
Schwarz et al.

(10) Patent No.: US 7,887,782 B2
(45) Date of Patent: Feb. 15, 2011

(54) RADIOTHERAPEUTIC FORMULATIONS CONTAINING 224RA AND A METHOD FOR THEIR PRODUCTION

(75) Inventors: Uwe Schwarz, Salzgitter (DE); Rolf Daniels, Salzgitter (DE)

(73) Assignee: Altmann Therapie GmbH & Co., Salzgitter (DE)

( * ) Notice: Subject to any disclaimer, the term of this patent is extended or adjusted under 35 U.S.C. 154(b) by 671 days.

(21) Appl. No.: 10/362,049

(22) PCT Filed: Aug. 7, 2001

(86) PCT No.: PCT/EP01/09121

§ 371 (c)(1),
(2), (4) Date: Jul. 9, 2003

(87) PCT Pub. No.: WO02/15943

PCT Pub. Date: Feb. 28, 2002

(65) Prior Publication Data

US 2004/0028606 A1 Feb. 12, 2004

(30) Foreign Application Priority Data

Aug. 21, 2000 (DE) ................ 100 40 771

(51) Int. Cl.
*A61K 51/00* (2006.01)
*A61M 36/14* (2006.01)
(52) U.S. Cl. ................ 424/1.11; 424/1.61
(58) Field of Classification Search ............. 424/1.11, 424/1.61
See application file for complete search history.

(56) References Cited

U.S. PATENT DOCUMENTS

| | | | |
|---|---|---|---|
| 3,993,538 A | * | 11/1976 | Lebowitz et al. ............ 376/195 |
| 4,663,129 A | | 5/1987 | Atcher et al. |
| 4,859,431 A | * | 8/1989 | Ehrhardt ................ 250/432 PD |
| 5,457,323 A | | 10/1995 | Geerlings |
| 5,854,968 A | * | 12/1998 | Horwitz et al. ................ 423/2 |

OTHER PUBLICATIONS

Delikan, O. Health Phys. 1978, 35, 21-24.*
Narbutt et al. (Appl. Radiat. Isot. 1998, 49, 89-91).*
Orhan Delikan; Preparation of $^{224}$Ra for Therapy of Ankylosing Spondylitis*; *Health Physics* vol. 35 (July) pp. 21-24 Pergamon Press Ltd., 1978.
Radioaktives Arzneimittel; Gebrauchsinformation und Fachinformation; pp. 1-6, No English translation.
Alberding, A. et al., "Wirksamkeit und Vertraglichkeit von Radiumchlorid in der Behandlung der ankylosierenden Spondylitis," Z Rheumatol 2006, 65:245-251.

* cited by examiner

*Primary Examiner*—Michael G Hartley
*Assistant Examiner*—Melissa Perreira
(74) *Attorney, Agent, or Firm*—Sam K. Tahmassebi; TechLaw LLP

(57) ABSTRACT

The invention relates to novel radiotherapeutic formulations containing $^{224}$Ra and methods for their production. The invention discloses, in particular, radiotherapeutic formulations comprising at least one salt of the isotope $^{224}$Ra, which are characterized in that the content of other radionuclides, in particular, the respective content of certain longeval radionuclides does not exceed a specific numerical value in mBq/g. The invention also relates to a method for producing radiotherapeutic formulations of this type, which is characterized by the following steps: after at least one centrifugation of an aqueous suspension of the compound $^{228}$Th(OH)$_4$ and optionally after the resuspension of the raw sediment obtained in said centrifugation, the precipitated $^{228}$Th(OH)$_4$ sediment is separated. The supernatant solution of a $^{224}$Ra salt that has been obtained is subsequently subjected to sterile filtration and is then made up to the required dose. Finally, said solution is sterilized and bottled in ampoules in a manner known per se.

20 Claims, No Drawings

RADIOTHERAPEUTIC FORMULATIONS CONTAINING 224RA AND A METHOD FOR THEIR PRODUCTION

SPECIFICATION

This invention relates to novel, $^{224}$Ra-containing, radiotherapeutic formulations and processes for their production.

Ankylosing spondylitis (Bechterew's disease) is a clinical picture which has been known for a long time and which is accompanied by degenerative ossification processes of the spinal column and residual spinal curvature. The use of formulations based on salts of the radioisotope $^{224}$Ra for treatment of this disease is prior art which likewise has been known for decades. Thus Orhan Delikan in the literature citation Health Physics, Vol. 35 (July), pp. 21-24, Pergamon Press Ltd., 1978 describes that the limitation of the content of contaminating radioisotopes, such as for example the especially long-lived, alpha particle-emitting nuclides $^{228}$Th, $^{226}$Ra, $^{228}$Ra or $^{227}$Ac, acquires decisive importance for the success or failure of one such therapy. These contaminants are easily incorporated by the patient into the bone substance and accumulated there as a result of their pronounced structure-chemical isomorphism with the isotope $^{224}$Ra; this works against the actual radiotherapy or is at least associated with considerable side effects which burden the patient. Since production of the therapeutic isotope $^{224}$Ra proceeding from the isotope $^{228}$Th takes place with emission of an alpha particle ($^{4}$He), both prior purification of the parent material $^{228}$Th which has been used and also subsequent separation of the resulting product isotope $^{224}$Ra as thoroughly as possible from the reaction mixture with respect to the desired production of a therapeutic agent which is as effective as possible without undesirable peripheral effects and side effects acquire great importance.

According to the prior art the parent material $^{228}$Th is purified by ion exchange chromatographic separation of the aforementioned disruptive isotopes. Then precipitation of the $^{228}$Th as a poorly soluble hydroxide and washing of the sediment take place. After the daughter isotope $^{224}$Ra is newly formed over the course of roughly 5 to 10 days, then extraction of the $^{228}$Th which is present as the hydroxide in an aqueous solution takes place using a calcium chloride solution; after being repeated several times this leads to a more or less pure aqueous ($^{224}$Ra)RaCl$_2$ solution.

The two above described purification steps are however described as extremely unsatisfactorily by specialists. Thus the aforementioned literature citation from Delikan in the paragraph between pages 22 and 23 remarks that $^{228}$Th extraction is "very critical" since here different boundary conditions and process parameters which are difficult to adjust must be watched at the same time; adherence to them subsequently makes it difficult or impossible to effectively carry out the purification step even for the best trained and equipped individual skilled in the art. On page 23, left column, at the start of the first complete paragraph it is moreover noted that $^{224}$Ra-containing formulations which have been produced using one such process of the prior art generally contain a still measurable residual content of the aforementioned, long-lived radionuclides in spite of all purification steps; this can be attributed to the fact that the salts of these nuclides are not completely insoluble and thus in part even after extraction of the $^{228}$Th remain in the therapeutically used $^{224}$Ra formulation.

Thus, according to the prior art there is a demand for a radiotherapeutic formulation for treatment of ankylosing spondylitis (=Bechterew's disease) which a priori avoids the above described defects of the formulations of the prior art by a degree of purity which is higher than in known formulations, especially by a much lower content of the above described long-lived nuclides $^{228}$Th, $^{226}$Ra, $^{228}$Ra or $^{227}$Ac.

It has unexpectedly been found that this object is achieved by a novel therapeutic formulation which contains the $^{224}$Ra isotope.

This formulation as claimed in the invention comprises at least one salt of the isotope $^{224}$Ra and is characterized in that the content of other radionuclides, especially the content of the radionuclides cited below, does not exceed the indicated numerical value for each:

| Radionuclide: | Maximum concentration (mBq/g) |
|---|---|
| $^{228}$Ra | 60 |
| $^{228}$Th | 30 |
| $^{210}$Pb | 30 |
| $^{226}$Ra | 30 |
| $^{238}$U | 20 |
| $^{231}$Pa | 60 |
| $^{227}$Ac | 10 |
| $^{232}$U | 50. |

According to one preferred embodiment the formulation as claimed in the invention is characterized in that the content of other radionuclides, especially the content of the radionuclides which are listed below, does not exceed the indicated numerical value for each:

| Radionuclide: | Maximum concentration (mBq/g) |
|---|---|
| $^{228}$Ra | 26 |
| $^{228}$Th | 3.6 |
| $^{210}$Pb | 23 |
| $^{226}$Ra | 29 |
| $^{238}$U | 19 |
| $^{231}$Pa | 55 |
| $^{227}$Ac | 9.3 |
| $^{232}$U | 20. |

According to one especially preferred embodiment the formulation as claimed in the invention is characterized in that the content of other radionuclides, especially the content of the radionuclides which are listed below, does not exceed the indicated numerical value for each:

| Radionuclide: | Maximum concentration (mBq/g) |
|---|---|
| $^{228}$Ra | 22 |
| $^{228}$Th | 3.3 |
| $^{210}$Pb | 17 |
| $^{226}$Ra | 26 |
| $^{238}$U | 15 |
| $^{231}$Pa | 55 |
| $^{227}$Ac | 8.4 |
| $^{232}$U | 5. |

According to another preferred embodiment the formulation as claimed in the invention is characterized in that the salt of the radionuclide $^{224}$Ra is radium chloride ($^{224}$RaCl$_2$). Moreover, the formulation as claimed in the invention preferably comprises an isotonic solution, especially preferably of a calcium salt, especially calcium chloride.

The formulation as claimed in the invention is produced using a process which is characterized in that the process steps (a) to (d) which are described below are carried out:
(a) At least one-time centrifuging of an aqueous suspension of the compound $^{228}$Th(OH)$_4$, optionally after resuspension of the resulting raw sediment;
(b) Separation of the $^{228}$Th(OH)$_4$ sediment which has been precipitated after step (a);
(c) Sterile filtration and subsequent bottling of the desired dose of the supernatant solution of the $^{224}$Ra salt which was obtained after step (b);
(d) Sterilization of the bottling obtained after step (c) in the conventional manner.

One preferred embodiment of the process as claimed in the invention is characterized in that the centrifuging in step (a) is carried out twice and the resulting precipitate is resuspended afterwards using an isotonic aqueous solution, especially preferably of a calcium salt, especially a 1.14% by weight CaCl$_2$ solution.

Another especially preferred embodiment of the process as claimed in the invention is characterized in that centrifuging is carried out in step (a) with a rotational speed corresponding to a centrifugal acceleration of 2000 g for 10 minutes.

Another preferred embodiment of the process as claimed in the invention is characterized in that the separation in step (b) is carried out by suction and filtration.

Another preferred embodiment of the process as claimed in the invention is characterized in that sterile filtration in step (c) is carried out using a known sterile material, especially preferably using a material based on a fluorine-containing organic service polymer or an optionally modified and/or derivatized polysaccharide.

One especially preferred embodiment of the process as claimed in the invention is characterized in that the sterile filter material is cellulose, cellulose acetate or polytetrafluorethylene, especially preferably cellulose acetate.

One preferred embodiment of the process as claimed in the invention is characterized in that the sterile filter material has a pore size in the range from roughly 0.01 micron to 10 microns, especially preferably in the range from roughly 0.2 micron to 5 microns and especially roughly 0.2 microns.

Another preferred embodiment of the process as claimed in the invention is characterized in that the sterilization step (d) is carried out using a conventional autoclave, especially preferably at a temperature of roughly 121° C. for roughly 20 minutes.

Another preferred embodiment of the process as claimed in the invention is characterized in that the therapeutic salt of the radionuclide $^{224}$Ra is radium chloride ($^{224}$RaCl$_2$).

This invention is described in greater detail in the following text sections using the corresponding representative embodiments.

EMBODIMENTS

1. Production of [$^{228}$Th] Thorium Hydroxide

Production of $^{228}$Th

Production of $^{228}$Th takes place proceeding from $^{231}$Pa by the $^{231}$P(n y) $^{232}$Pa reaction. The $^{232}$Pa which has been formed in this reaction decays first into $^{232}$U and then into $^{228}$Th. For production, the daughters of protactinium pentoxide were removed from it, the protactinium pentoxide was sealed in quartz vials and irradiated in a reactor. After a decay time of a few weeks ion exchange chromatographic separation of the $^{232}$U($t_{1/2}$=72 years) took place; its was captured as the chloride, dried and stored in order to obtain $^{228}$Th.

This material was dissolved in HNO$_3$ and passed via an anion exchange column. Under these conditions thorium is bound as [Th(NO$_3$)$_6$]$^{2-}$ on the column and the daughters of $^{228}$Th and $^{232}$U were washed from the column using HNO$_3$. Then $^{228}$Th was washed from the column with 0.5 m HCl. After determining the concentration, this solution was transferred to glass vessels and dried.

Production of [$^{228}$Th] Thorium Hydroxide

1. The [$^{228}$Th] thorium chloride is taken up using the carrier solution [$^{232}$Th] thorium nitrate pentahydrate in hydrochloric acid 10%, Ph. Eur.*) in component steps in the primary container and transferred into a 50 ml centrifuge tube.
2. The insoluble thorium hydroxide is precipitated from this solution with ammonia solution (26%). Calcium chloride solution is added to 30 ml and centrifuging is done at 2000 g for 10 minutes. The addition of [$^{232}$Th] thorium nitrate pentahydrate as the carrier in step 1 guarantees the formation of relatively large amounts of precipitate which can be quantitatively separated by centrifuging, and minimizes adsorption effects of $^{228}$Th.
3. The supernatant is carefully suctioned through a glass suction filter. The residue is mixed with calcium chloride solution 1.14% and after stirring with a magnetic stirrer, centrifuged again. This washing step is repeated once more in order to completely remove traces of unsedimentable thorium hydroxide which may be present. During the last suction the entire supernatant is removed as much as possible.
4. The raw sediment which has been obtained in this manner is dried.
5. The dried raw sediment is resuspended in calcium chloride solution 1.14% and stored in a closed centrifuge tube.

2. Production of [$^{224}$Ra] Radium Chloride

Production of [$^{224}$Ra] radium chloride takes place in 4 stages. Stages 1-3 are carried out in a gastight box with lead shielding and remote control. The inlet air is filtered sterile by a filter of suspended matter of class S. The required articles can be placed in the box via airlocks.

Stage 1 Extraction and Centrifuging

The soluble [$^{224}$Ra] radium chloride is desorbed with calcium chloride solution from the insoluble [$^{228}$Th] thorium hydroxide and separated by centrifuging.

This step is repeated several times. The supernatants are withdrawn after each centrifuging and then combined into the batch stock solution. The production suspension is resuspended and stored.

Stage 2 Filling of Injection Vials with Doses

To determine the [$^{224}$Ra] radium chloride concentration a radioactivity check measurement of an aliquot of the batch stock solution is taken.

Based on the determined activity concentration the injection vials are filled with the batch stock solution and accordingly calcium chloride solution (1.14%) using a dual syringe-dilutor with sterile syringe end filters. If filling is done for several calibration times on the same day, the amount of the batch stock solution to be added is changed according to the decay of the radium-224 ($T_{1/2\,phys}$=3.66 days) and the amount of calcium chloride solution is increased to make 1.1 ml. The vials are then closed and sealed.

Stage 3 Sterilization

The preparation is sterilized at 121° C. for 20 minutes in a laboratory autoclave.

Stage 4 Labelling of the Outer Containers and Packaging

After sterilization, the vials which were already labelled before filling are removed from the production box and packaged.

The invention claimed is:

1. A radiotherapeutic formulation comprising at least one salt of the isotope $^{224}$Ra, wherein the content of radionuclides listed below does not exceed the indicated numerical value for each:

| Radionuclide: | Maximum concentration (mBq/g) |
|---|---|
| $^{228}$Ra | 26 |
| $^{228}$Th | 3.6 |
| $^{210}$Pb | 23 |
| $^{226}$Ra | 29 |
| $^{238}$U | 19 |
| $^{231}$Pa | 55 |
| $^{227}$Ac | 9.3 |
| $^{232}$U | 20. |

2. The radiotherapeutic formulation of claim 1, wherein the content of radionuclides listed below does not exceed the indicated numerical value for each:

| Radionuclide: | Maximum concentration (mBq/g) |
|---|---|
| $^{228}$Ra | 22 |
| $^{228}$Th | 3.3 |
| $^{210}$Pb | 17 |
| $^{226}$Ra | 26 |
| $^{238}$U | 15 |
| $^{231}$Pa | 55 |
| $^{227}$Ac | 8.4 |
| $^{232}$U | 5. |

3. The radiotherapeutic formulation of claim 1, wherein the salt of the radionuclide $^{224}$Ra is radium chloride ($^{224}$RaCl$_2$).

4. The radiotherapeutic formulation of claim 1, wherein the formulation comprises an isotonic.

5. Process for producing a radiotherapeutic formulation comprising at least one salt of the isotope $^{224}$Ra, wherein the process comprises the steps of:
   (a) Obtaining $^{228}$Th from $^{232}$U;
   (b) Binding the $^{228}$Th of step (a) as the anion [$^{228}$Th(NO$_3$)$_6$]$^2$ on an anion exchange column;
   (c) Washing the bound $^{228}$Th of step (b) from the anion exchange column using a solution of HCl:
   (d) Precipitating the resulting $^{228}$Th of step (c) as $^{228}$Th(OH)$_4$;
   (e) Resuspending the $^{228}$Th(OH)$_4$ using an aqueous solution comprising 1.14% by weight CaCl$_2$ and at least one-time centrifuging the resulting aqueous suspension; and
   (f) Sterile filtration and subsequent bottling of the desired dose of the supernatant solution of the centrifugation step in step (e);
   wherein the content of $^{228}$Th in the formulation does not exceed 3.6 mBq/g, and wherein the content of $^{227}$Ac in the formulation does not exceed 9.3 mBq/g.

6. The process of claim 5, wherein centrifuging is carried out in step (e) with a rotational speed corresponding to a centrifugal acceleration of 2000 g for 10 minutes.

7. The process of claim 5, wherein sterile filtration in step (f) is carried out using a known sterile filter material.

8. The process of claim 7, wherein the sterile filter material is cellulose, cellulose acetate or polytetrafluorethylene.

9. The process of claim 7, wherein the sterile filter material has a pore size in the range from roughly 0.01 micron to 10 microns.

10. The process of claim 5, further comprising the step of sterilization of the bottled dose obtained after step (f) using a conventional autoclave.

11. The process of claim 5, wherein the therapeutic salt of radionuclide $^{224}$Ra is radium chloride ($^{224}$RaCl$_2$).

12. A method of treating ankylosing spondylitis (Bechterew's disease) comprising administering the radiotherapeutic formulation of claim 1 to a patient in need of such a treatment.

13. The radiotherapeutic formulation of claim 2, wherein the salt of the radionuclide $^{224}$Ra is radium chloride ($^{224}$RaCl$_2$).

14. The radiotherapeutic formulation of claim 2, wherein the formulation comprises an isotonic.

15. The radiotherapeutic formulation of claim 3, wherein the formulation comprises an isotonic.

16. The process of claim 7, wherein the sterile filter material is based on a fluorine-containing organic service polymer or an optionally modified and/or derivatized polysaccharide.

17. The process of claim 8, wherein the sterile filter material is cellulose acetate.

18. The process of claim 9, wherein the sterile filter material has a pore size in the range from roughly 0.2 micron to 5 microns.

19. The process of claim 18, wherein the sterile filter material has a pore size of roughly 0.2 microns.

20. The process of claim 10, wherein the sterilization step (d) is carried out at a temperature of roughly 121° C. for roughly 20 minutes.

* * * * *